(12) United States Patent
Rose et al.

(10) Patent No.: US 7,709,221 B2
(45) Date of Patent: May 4, 2010

(54) BIOSENSOR WITH INORGANIC-ORGANIC HYBRID POLYMER COATING

(75) Inventors: Klaus Rose, Kitzingen (DE); Roberto Fernandez Lafuente, Madrid (ES); Jose Manuel Guisan, Madrid (ES); Lorena Betancor, Montevideo (UY); Nicole Jaffrezic, Ecully (FR); Sergei Dzyadevych, Kiev (UA)

(73) Assignees: Fraunhofer Gesellschaft zur Forderung der angewandten Forschung e.V., Munich (DE); Institute of Catalysis, Madrid (ES); Ecole Centrale de Lyon, Ecully Cedex (FR)

( * ) Notice: Subject to any disclaimer, the term of this patent is extended or adjusted under 35 U.S.C. 154(b) by 517 days.

(21) Appl. No.: 11/598,935

(22) Filed: Nov. 14, 2006

(65) Prior Publication Data

US 2007/0161069 A1    Jul. 12, 2007

(30) Foreign Application Priority Data

Nov. 17, 2005    (EP) .................................. 05025177

(51) Int. Cl.
    *C12Q 1/54*    (2006.01)
(52) U.S. Cl. ...................... 435/14; 435/287.9; 435/817; 204/403.11
(58) Field of Classification Search .................. 435/14, 435/287.9, 817; 204/403.11
See application file for complete search history.

(56) References Cited

U.S. PATENT DOCUMENTS

| | | | |
|---|---|---|---|
| 4,974,929 A | 12/1990 | Curry | |
| 5,994,091 A * | 11/1999 | Attridge et al. | 435/7.72 |
| 2003/0164024 A1 | 9/2003 | Mitsubayashi et al. | |
| 2004/0101741 A1 * | 5/2004 | Minteer et al. | 429/43 |
| 2005/0095466 A1 | 5/2005 | Minteer et al. | |
| 2005/0113658 A1 * | 5/2005 | Jacobson et al. | 600/342 |
| 2009/0089999 A1 * | 4/2009 | Say et al. | 29/829 |
| 2009/0166223 A1 * | 7/2009 | Forrow et al. | 205/777.5 |

FOREIGN PATENT DOCUMENTS

EP        1496126 A1        1/2005

WO        WO 2005/093888 A2        10/2005

OTHER PUBLICATIONS

Betancor L. et al. Advantages of the Pre-Immobilization of Enzymes on Porous Supports for Their Entrapment in Sol-Gels. Biomacromolecules 6(2)1027-1030, 2005.*
Warren S. et al. Investigation of Novel Mediators for a Glucose Biosensor Based on Metal Picolinate Complexes. Bioelectrochemistry 67(1)23-35, 2005.*
Wu X. et al. A Glucose Biosensor with Enzyme Entrapped Sol-Gel and an Oxygen Sensitive Optode Membrane. The Analyst (125(1)157-162, 2000.*
Scheper T. et al. Optical Sensors for Biotechnological Applications. Biosensors & Bioelectronics 9(1)73-83, 1994.*
Wolfbeis O. et al. Sol-Gel Based Glucose Biosensors Employing Optical Oxygen Transducers . . . Biosensors & Bioelectronics 15(1-2)69-76, 2000.*
Anders et al., *Biosensors & Bioelectronics*, 9: 73-83 (1994).
Betancor et al., *Biomacromolecules*, 6:1027-1030 (2005).
Campuzano et al., *Bioelectrochemistry*, 63: 199-206 (2004).
Compagnone et al., *Biosensors & Bioelectronics*, 13: 875-880 (1998).
Luong et al., *Biosensors & Bioelectronics*, 6: 547-554 (1991).
Warren et al., *Bioelectrochemistry*, 67: 23-35 (2005).
Wolfbeis et al., *Bisensors & Bioelectronics*, 15: 69-76 (2000).
Wu et al., *Analyst*, 125: 157-162 (2000).
Chang-Yen et al., *Proc. of SPIE*, 5345[1]: 98-107 (2003).
Choudhury et al., *J. Appl. Phys.*, 96[5]: 2949-2954 (2004).
Kotzian et al, *Analytical Letters*, 38[7]: 1099-1113 (2005).
Krihak et al., *SPIE*, 2293: 88-98 (1994).
Li et al., *Analytica Chimica Acta*, 353[2-3]:263-273 (1997).
Martin et al., *Biosensors & Bioelectronics*, 12[6]: 479-489 (1997).
Topcagic et al., *Polymeric Materials: Science & Engineering*, 92: 201-203 (2005).
Young et al., *Proc. of SPIE*, 5855: 431-434 (2005).
Xu et al., *Biosensors & Bioelectronics*, 21[3]: 455-461 (2005).

* cited by examiner

*Primary Examiner*—Ralph Gitomer
(74) *Attorney, Agent, or Firm*—Leydig, Voit & Mayer, Ltd.

(57) ABSTRACT

The present invention relates to a biosensor comprising a substrate with a coating system in which a Ruthenium complex and an enzyme is integrated. The enzyme is able to convert bioproducts, e.g. glucose, fructose or glycerol. The depletion of oxygen during these converting reactions can be monitored via the fluorescence of the Ruthenium complex. The inventive biosensor can be used in biotechnological processes, e.g. the synthesis of biofuels.

15 Claims, 3 Drawing Sheets

BIOSENSOR WITH INORGANIC-ORGANIC HYBRID POLYMER COATING

CROSS REFERENCE TO A RELATED APPLICATION

This application claims the benefit of European Patent Application No. 05 025 177.6, filed Nov. 17, 2005, the disclosure of which is incorporated by reference.

The present invention relates to a biosensor comprising a substrate with a coating system in which a Ruthenium complex and an enzyme is integrated. The enzyme is able to convert bioproducts, e.g. glucose, fructose or glycerol. The depletion of oxygen during these converting reactions can be monitored via the fluorescence of the Ruthenium complex. The inventive biosensor can be used in biotechnological processes, e.g. the synthesis of biofuels.

The economic realities of productivity, quality and reliability for industrial societies are placing major demands on manufacturing technologies. In order to meet both present and anticipated requirements, new and improved methods are needed. In the case of sensors optic, electronic or opto-electronic components have been developed to improve the effectivity.

The monitoring of industrial biotechnological reactions is becoming increasingly important for food and pharmaceutical industries. In particular the monitoring of bio-reactants such as glucose, fructose and glycerol in biotechnological processes is becoming increasingly important in industrial sectors such as: synthesis of bio-fuels, food and drink industry, pharmaceuticals or waste processing.

Data required for process control in many industries is currently obtained by taking samples and analysing them remotely. The resulting time delay can be critical for achieving optimum process control especially in just-in-time-production.

The concentrations of bio-reactants to be measured are low or they are not suitable for direct detection, so that, in general, the detection sensitivity needs to be enhanced by applying a suitably designed transducer.

There are many forms of appropriate transducers, however, most are not suited to the direct measurement of bio-reactants such as glucose, fructose and glycerol in bio-reactors because they are adversely affected by many factors such as pH and temperature. The small dimensions of fibre-optic sensors make local sensing of target analytes possible. The knowledge of concentration profiles within the whole volume is required for optimal design and scale-up of the reactors.

The most frequently used approaches are the immobilisation of chemical and biological transducers (molecules or compounds) at the detection site (the physical transducer) by chemical bonding or entrapment in polymer, gel or glass matrices. The physical transducer produces an electrical signal in response to changes in the electrical and/or optical properties of the chemical/biological transducer due to its interaction with the analyte.

Many types of transducers based on electrical principles (including ion-sensitive electrodes, ion-sensitive field effect transistors, amperometric electrodes), optical principles (absorbance- and fluorescence-based fibre-optic and integrated-optic waveguides, surface plasmons, optical interferometers and microscopy), thermal principles (calorimetry), acoustic principles (surface waves attenuation) have been used in building of chemical sensors and biosensors.

Fibre-optic waveguides demonstrated their advances in a number of chemical and biological sensors. They are compact, flexible to use, immune to electromagnetic fields, and exhibit good biocompatibility. Hence they are suitable for on-line monitoring of processes in harsh environment (T. Scheper, C. Müller, K. D. Anders, F. Eberhardt, F. Plotz, C. Schelp, O. Thordsen, K. Schügerl, "Optical sensors for biotechnological applications", Biosensors & Bioelectronics 9 (1994), 73).

In extrinsic sensors, optical fibres are used only for the transport of light to and from the detection site, which is located, for example, in the reaction vessel. In intrinsic sensors the detection site is created directly in the fibre structure on the fibre tip, fibre core or the fibre cladding. The phase and amplitude of the light transmitted by the fibre changes at the detection site accordingly to analyte-induced changes in optical properties of the transducing element. Main trust of the current work is the development of transducers based on fluorescence.

Several companies in the EC and USA produce sensors applicable for medical purposes or bioprocess monitoring. Most of these sensors are based on amperometric interrogation of biotransducers such as enzymes immobilised on membranes. These sensors can detect substances such as glucose, lactose, galactose or choline in $10^{-3}$ to $10^{-6}$ mM concentrations (J. H. T. Luong, C. A. Groom, K. B. Male, "The potential role of biosensors in the food and drink Industries", Biosensors & Bioelectronics 6 (1991) 547). Some of these sensors are generally accepted as providing a standard method for determining glucose and sucrose. Examples have been included in following Tab. Optical biosensors based on surface plasmon resonance are available from Biacore.

TAB 1

| Analyte | Micro-organism | Transducer/ Immobilisation | Detection Limit |
| --- | --- | --- | --- |
| Alcohol | Candida vini | Oxygen electrode (porous acetyl cellulose filter) | $2 \times 10^{-2}$-$2 \times 10^{-1}$ mM |
| Glucose | A. niger (glucose oxidase) | Oxygen electrode (entrapment in dialysis membrane) | >1.75 mM |
| Glucose, sucrose, lactose | G. oxydans (D-glucose dehydrogenase), S. cerevislae (Invertase), K.marxlanus (β-galactosidase) | Oxygen electrode (gelatine) | Up to 0.0.8 mM |
| Sugars (glucose) | Psychrophilic D. radiodurans | Oxygen electrode (agarose) | 0.03-0.55 mM |
| Short chain fatty acids in milk (butyric acid) | A. nicotianae (acyl-CoA oxidase) | Oxygen electrode (Polyvinyl alcohol) | 0.11-17 mM |
| Short chain fatty acids in milk (butyric acid) | A. nicotianae (acyl-CoA oxidase | Oxygen electrode (Ca-alginate) | 9.5-165.5 µM |
| Phosphate | Chlorella vulgaris | Oxygen electrode (polycarbonate membrane) | 8.70 mM |

TAB 1-continued

| Analyte | Micro-organism | Transducer/ Immobilisation | Detection Limit |
|---|---|---|---|
| $CO_2$ | $CO_2$ utilising autotropic bacteria (*Pseudomonas*) | Oxygen electrode (bound on cellulose nitrate membrane) | 0.2-5 mM |
| Vitamin B-6 | *S. urvarum* | Oxygen electrode (adsorption on cellulose nitrate membrane) | 0.5-2.5 ng/ml |
| Vitamin B-12 | *E. coli* | Oxygen electrode (trapped in porous acetyl cellulose membrane) | $5\text{-}25 \times 10^{-9}$ mM |
| Peptides (aspartame) | *B. subtills* | Oxygen electrode (filter paper strip and dialysis membrane) | 0.07 ... 0.6 mM |
| Phenylalanine | *P. vulgaris* (Phenylalanine deaminase) | Amperemetric oxygen electrode (Ca-alginate) | $2.5 \times 10.2^{-2}\text{-}2.5$ mM |
| Pyruvate | *Streptococcus faecium* (Pryuvate dehydrogenase complex) | $CO_2$ gas sensing electrode (direct immobilisation on sensor membrane) | 0.22-32 mM |
| Tyrosine | *A. phenologenes* (Tyrosine-phenol lyase) | $NH_3$ gas sensing electrode (direct immobilisation on sensor membrane) | $8.2 \times 10.2^{-2}\text{-}1.0$ mM |
| Enalapril maleate (angiotensin) | *B. subtills* | Oxygen electrode | |

The sensors developed for these purposes are mostly based on amperometry with an oxygen electrode or hydrogen peroxide electrode. The linear range of these electrodes can be limited by low oxygen concentrations, changes in response resulting from variations in ambient oxygen concentrations and the deactivation of enzyme by the hydrogen peroxide produced. Furthermore, usefulness of these electrodes in many biological applications is also limited by their sensitivity to stirring and a fact that they consume oxygen. Other practical problems include limited range of sterilisation methods due to the fragile construction of the electrochemical sensors.

The development of fibre-optic sensors usually requires special components and structures, which, in many cases, are not commercially available at reasonable prices. This situation becomes even more critical if special optical fibres are necessary for the development, because such fibres are not produced by large manufacturers who view the market for these fibres as far too narrow. Furthermore, there is a lack of optimised combinations of specially structured fibres, claddings, transducers and detection instrumentation. This is regarded to be the main reason why currently sensor users prefer sensors based on electrochemical technologies instead of fibre-optic sensors and why fibre-optic sensors potentially useful for bioprocess monitoring are discussed mainly in scientific papers. The proposed project aims to overcome the above disadvantages and to make fibre-optic biosensors available.

Optical sensors have advantages for chemical and biological measurement due to compactness, flexibility, immunity to electromagnetic fields and biocompatibility. Hence they are suitable for on-line monitoring of processes in harsh environments. In extrinsic sensors, optical fibres are used only for the transport of light to and from the detection site (e.g. a glass slide), which is located, for example, in the reaction vessel. In intrinsic sensors the detection site is created directly in the fibre structure on the fibre tip, fibre core or the fibre cladding.

Thus, proceeding from the above, it was the object of the present invention to overcome the above-mentioned disadvantages of the sensors known from the prior art and to provide a biosensor which is capable of monitoring biotechnological processes based on fibre-optic systems.

This object is achieved by the biosensor having the features of claim 1. In claim 15, the inventive uses are mentioned. Preferred embodiments arise from the further dependent claims.

According to the present invention a biosensor is provided comprising a substrate with at least one coating. The coating consists of an inorganic-organic hybrid polymer as a matrix for at least one Ruthenium complex. Further, the biosensor comprises at least one enzyme for the conversion of bioproducts.

DETAILED DESCRIPTION OF THE INVENTION

Figure 1:
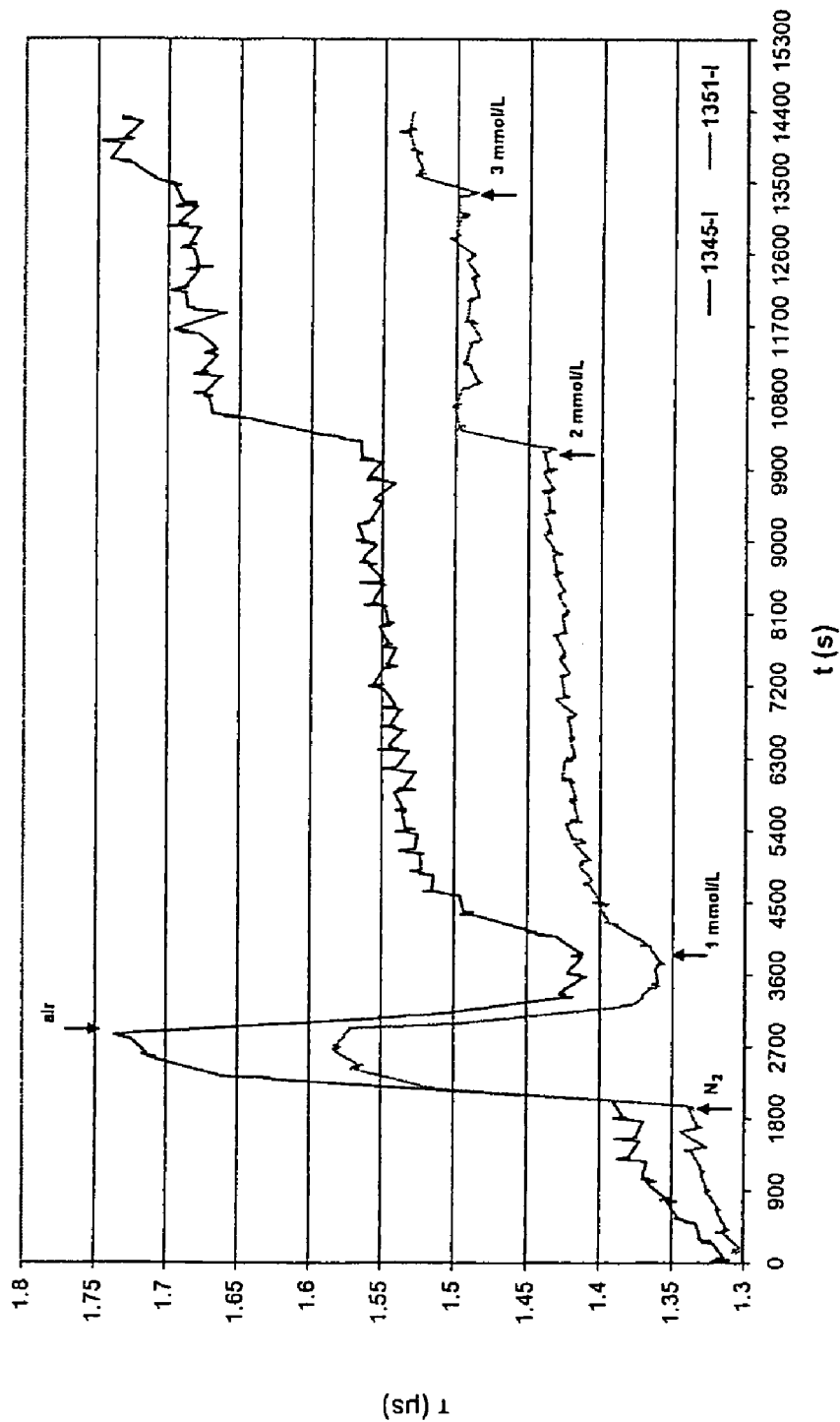
FIG. 1 depicts fluorescence lifetime (μs) of Ru complex as a function of reaction time(s) in response to an aerobic (in air)—anaerobic (in nitrogen) change of conditions and in response to an increase of glucose concentration. For FIG. 1 and FIG. 2, see Example 2.

The sensor described in this invention was designed for use with a transduction process as sensor reaction that uses an enzyme to convert bioproducts, e.g. glucose, fructose or glycerol in combination with oxygen detection. As an example the reaction of glucose to gluconic acid and of oxygen to hydrogen peroxide is outlined in the following equation.

Eqn. 1

The oxygen concentration is measured via the fluorescence of a Ruthenium complex, e.g. Dichlorotris(1,10-phenantroline)-ruthenium(II), incorporated in an inorganic-organic hybrid ORMOCER coating together with the immobilised enzyme. The fluorescence is therefore related to the depletion of oxygen, and thus the oxygen concentration present within the coating. Oxygen quenches the fluorescence of the Ruthenium complex.

The hybrid coating is applied onto an optical substrate to form a chemical-opto transducer layer. The substrate can be a microscope slide or lens, or the cladding layer of an optical fibre. The sensitivity of the sensor to glucose depends on the activity, homogeneity and successful immobilization of enzymes within the coating, in close contact with the Ruthenium complex fluorophores.

Thus, the enzyme/Ruthenium/ORMOCER® coating can be interrogated as part of an extrinsic optical fibre system, using a transmitting fibre to carry excitation light to the layer and a second fibre to collect the fluorescent light. In a further inventive alternative the enzyme/Ruthenium/ORMOCER® coating can be interrogated as the cladding layer of an intrinsic fibre sensor using evanescent field excitation.

Fluorescence quenching of the Ruthenium complex is measured via changes in the lifetime of fluorescence decay. Fluorescence is excited using blue LEDs.

The sensitive element consisting of glass substrate, e.g. glass slide or optical fibre, and sensitive layer can be built up in two modifications: a double layer structure and a single layer structure.

In the double layer structure the glass substrate is covered by a primary coating containing the Ruthenium complex and with a secondary coating containing the immobilised enzyme on the primary coating.

In the single layer structure the glass substrate is covered by a single coating containing both the Ruthenium complex and the enzyme.

In order to be industrially viable the systems have to be compatible with existing fibre optic and opto electronic technology. Hence the coatings need to be made from materials that are UV-curable.

The invention comprises the use of inorganic-organic hybrid polymers as liquid coating material. The principle of the formation of inorganic-organic hybrid polymers via sol-gel processing is the hydrolysis and condensation of organically functionalized alkoxysilanes as outlined in the following reaction scheme:

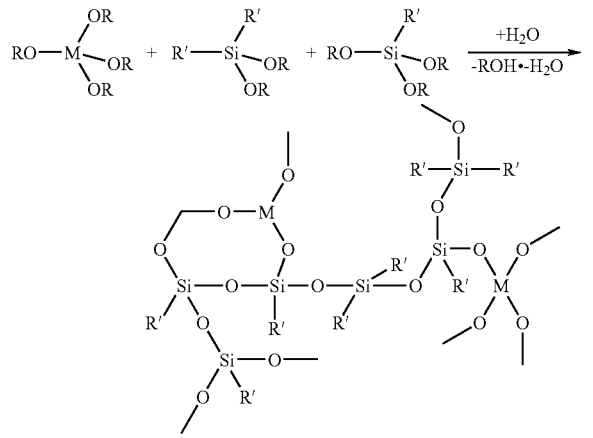

with
R = alkyl, e.g. methyl, ethyl
M = e.g. Si, Ti, Zr, Al
R' = non-reactive/functional or reactive/UV-polymerizable group with
R=alkyl, e.g. methyl, ethyl
M=e.g. Si, Ti, Zr, Al
R'=non-reactive/functional or reactive/UV-polymerizable group As a result of this reaction an inorganic, silica-like network or silicone-like chain as prepolymer is formed bearing functional organic groups R'.

The combination of organically substituted alkoxysilanes with alkoxy compounds of metals, e.g. $Si(OEt)_4$, $Ti(OEt)_4$, $Zr(OPr)_4$, $Al(O^sBu)_3$ will modify the inorganic part of the material by formation of the corresponding metal oxide structure. In this way very hard and highly densified materials are available which can be used as scratch resistant or barrier coatings. Examples of precursors for the formation of a pure inorganic glass-like or ceramic-like network are as follows:

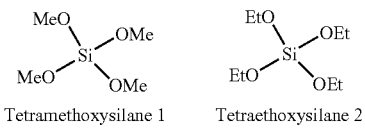

Tetramethoxysilane 1    Tetraethoxysilane 2

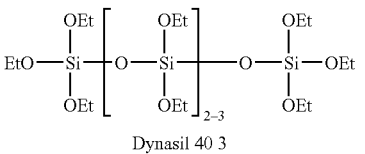

Dynasil 40 3

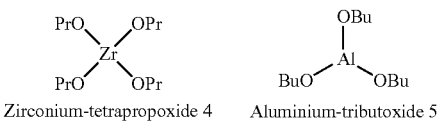

Zirconium-tetrapropoxide 4    Aluminium-tributoxide 5

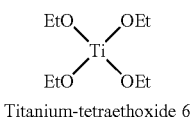

Titanium-tetraethoxide 6

The monomer compounds for the formation of a pure inorganic network may bear an organic complex ligand like acetic acid ethyl ester or methacrylic acid:

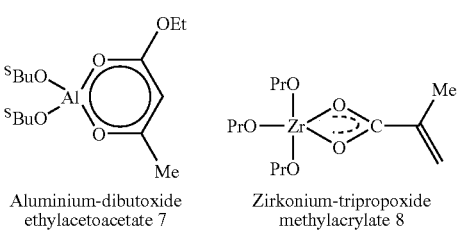

Aluminium-dibutoxide ethylacetoacetate 7    Zirkonium-tripropoxide methylacrylate 8

It is also possible to use an oligomer siloxane as inorganic crosslinker:

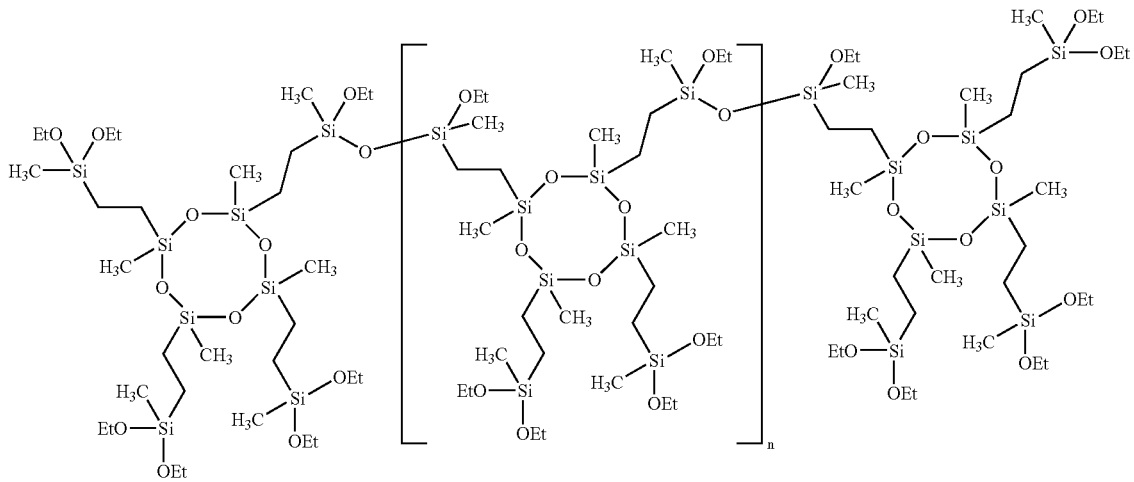

Bayresit VPLS 2331 9

Non-reactive groups R' act as network modifiers suitable for network functionalisation in order to introduce chemical properties to the coating. Examples of organically functionalised alkoxysilanes are given below:

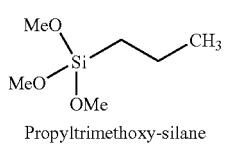

Propyltrimethoxy-silane

10

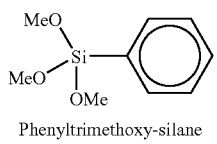

Phenyltrimethoxy-silane

11

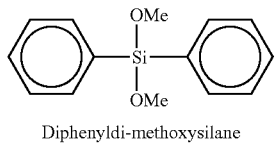

Diphenyldi-methoxysilane

12

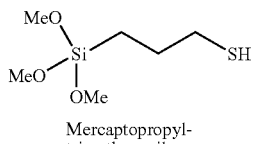

Mercaptopropyl-trimethoxysilane

13

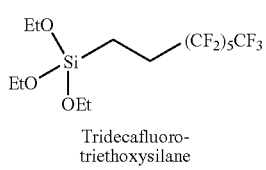

Tridecafluoro-triethoxysilane

14

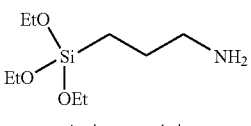

Aminopropyltri-ethoxysilane

15

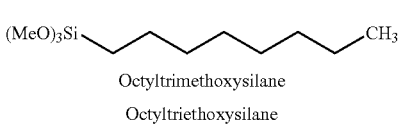

Octyltrimethoxysilane

Octyltriethoxysilane 16a
16b

Hexadecyltrimethoxysilane

17

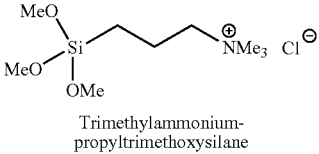

Trimethylammonium-propyltrimethoxysilane

18

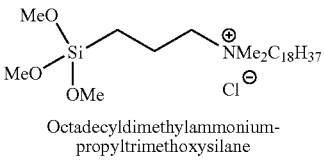

Octadecyldimethylammonium-propyltrimethoxysilane

19

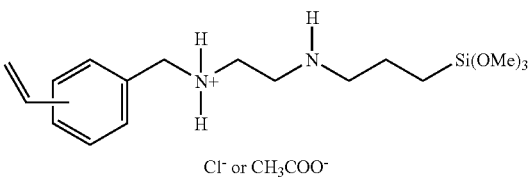

Cl⁻ or CH₃COO⁻

Vinylbenzyl ammoniumethyl aminopropyl-trimethoxysilane

20

-continued

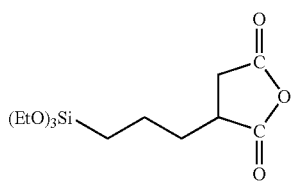
Succinic acid anhydride propyl triethoxysilane

In the case of reactive groups R' an additional organic polymer network can be formed by polymerization reactions of the reactive groups. Examples of monomer silanes with reactive and UV-curable groups are as follows:

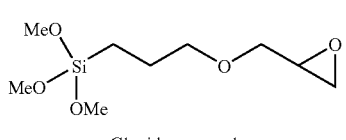
Glycidoxypropyl-
trimethoxysilane

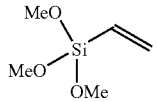
Vinyltrimethoxy-
silane

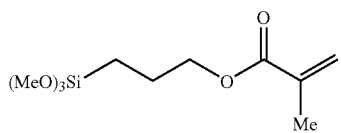
Methacryloxypropyl-
trimethoxysilane

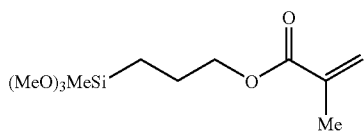
Methacryloxypropylmethyl-
Dimethoxysilane

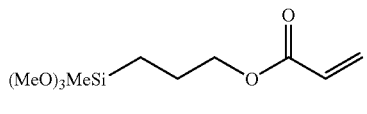
Acryloxypropylmethyl
Dimethoxysilane

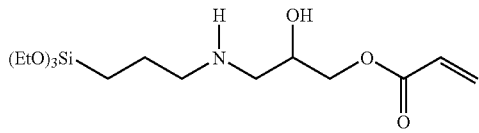
N-(3-Acryloxy-2-Hydroxypropyl)-
3-Aminopropyltri-ethoxysilane

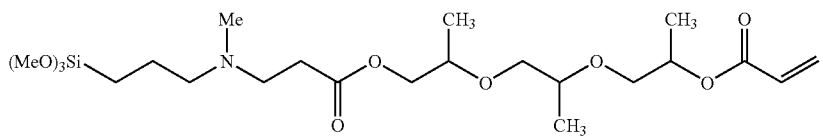
Tripropyleneglycolacrylate trimethoxysilane

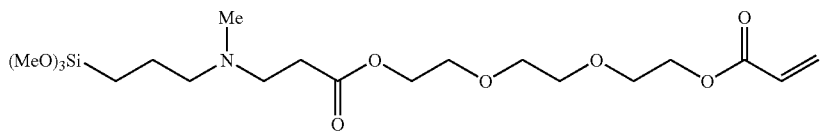
Triethyleneglycolacrylate trimethoxysilane

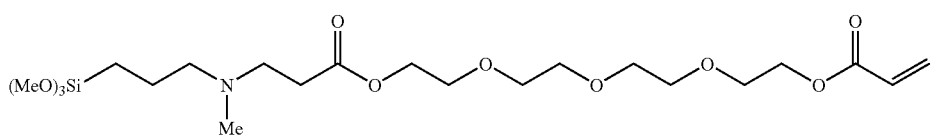
Tetraethyleneglycolacrylate trimethoxysilane

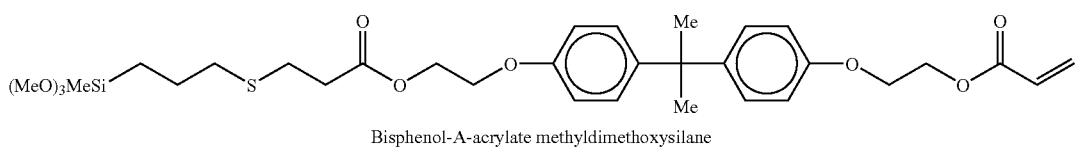
Bisphenol-A-acrylate methyldimethoxysilane

-continued

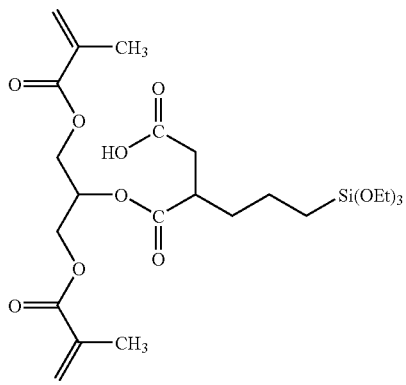

Glycerindimethacrylate triethoxysilane-a
(GDMA silane-a)

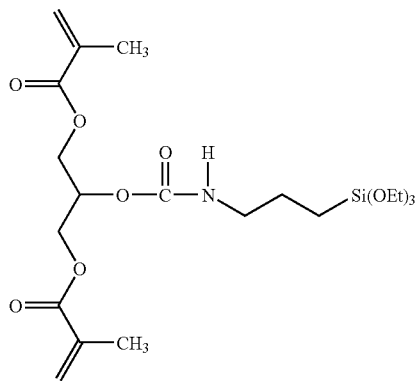

Glycerindimethacrylate triethoxysilane-b
(GDMA silane-b)

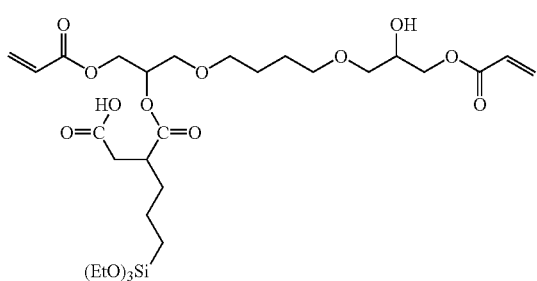

Butandiol-diglycidether-diacrylate triethoxysilane-a
(LR 8765 silane-a)

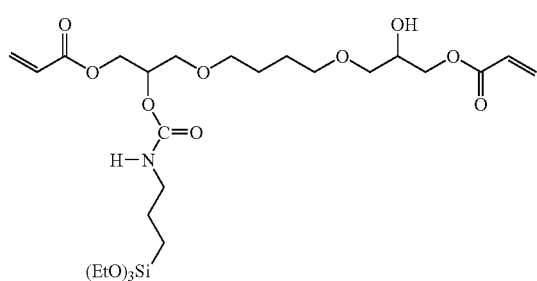

Butandiol-diglycidether-diacrylate triethoxysilane-b
(LR 8765 silane-b)

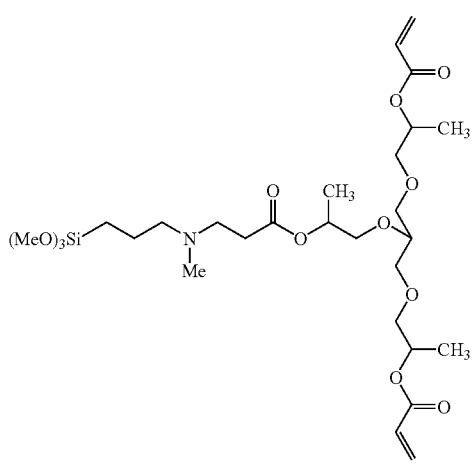

Propoxylated glyceryldiacrylate trimethoxysilane
(SR 9020 silane)

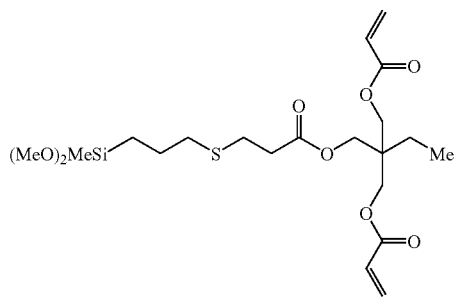

Trimethylopropanediacrylate methyldimethoxysilane
(TMPTA silane)

-continued

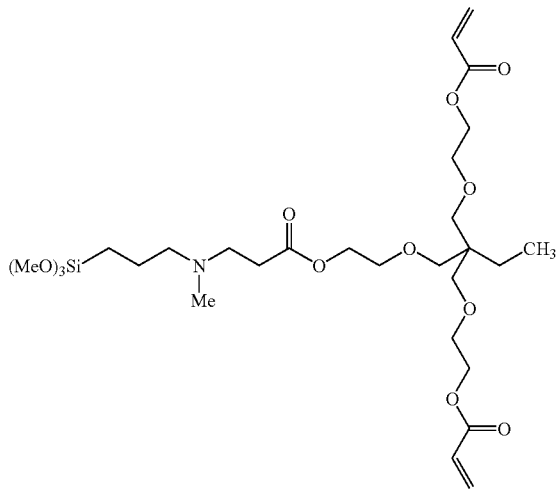

Ethoxylated trimethylolpropane diacrylate trimethoxysilane
(SR454 silane)

38

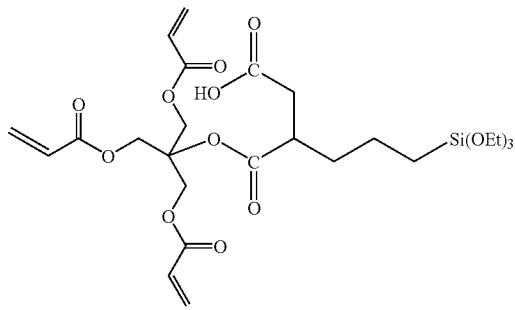

Pentaerythritoltriacrylate triethoxysilane-a
(PETA silane a)

39

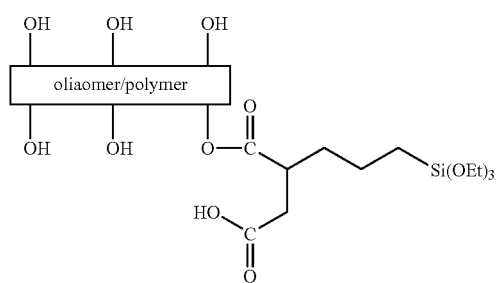

Pentaerythritoltriacrylate triethoxysilane-b
(PETA silane b)

40

Polymer based silanes are derived from acrylate copolymers. The general structure is as follows:

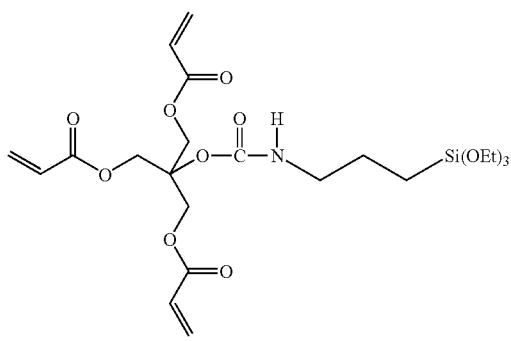

Oligomers or polymers are copolymers of hydroxyethylacrylate and n-butylacrylate 41

For glucose determination the enzyme glucose oxidase is used. The following commercially available enzymes can be used:

1. Glucose Oxidase from *Penicillium vitale* with activity 130 Units/mg (purchased from "Diagnosticum" Co., L'vov, Ukraine).
2. Glucose Oxidase from *Aspergillus niger* with activity 271 Units/mg (purchased from "Genzyme" Co, Kent, UK).
3. Glucose Oxidase from *Aspergillus niger* with activity 220 Units/mg (purchased from "Fluka Chemie GmbH", Buchs, Switzerland).
4. Glucose Oxidase from *Aspergillus niger* (type II S) with activity 16 Units/mg (purchased from "Sigma-Aldrich Chemie GmbH", Steinheim, Germany).
5. Glucose Oxidase from *Aspergillus niger* (type II S) with activity 47 Units/mg (purchased from "Sigma-Aldrich Chemie GmbH", Steinheim, Germany).

In the following examples glucose oxidase from *Penicillium vitale* with activity 130 Units/mg (GOD 130) was used.

Enzymes such as glucose oxidase can be used without any further modification. However, considering their moderate stability, in many instances it may be necessary to stabilize them for instance by covalent immobilization, physical adsorption, cross-linking, encapsulation or entrapment. This procedure may be necessary to prevent leakage of the enzymes from the matrix (coating) or to stabilize them against inactivation or even chemical decomposition during the several preparation steps of the incorporation and coating procedures. Immobilization in polymeric porous host matrices before incorporation into sensor layers is a convenient method for stabilization. The polymeric matrix must have a pore size adequate to allow the flow of substances to be detected to the enzyme in the pores and to prevent the elution of the enzyme.

Pre-immobilization of enzymes on porous supports is extensively described in the following paper: Lorena Betancor, Fernando Lopez-Gallego, Aurelio Hidalgo, Manuel Fuentes, Ondrej Podrasky, Gabriela Kuncova, Jose M. Guisan, Roberto Fernandez-Lafuente, Biomacremolecules 6 (2005) 1027-1030.

Suitable porous polymers can be styrene/divinylben-zene copolymer, polystyrene or polyacrylics, called "Sepabeads".

For Fructose determination the enzymes glucose isomerase, glucose oxidase and catalase can be used.

For Glycerol determination the enzymes glycerokinase, L-Glycerol 3-Phosphate and, catalase can be used.

Examples of Ruthenium complexes are as follows (other Ruthenium complexes are also possible):

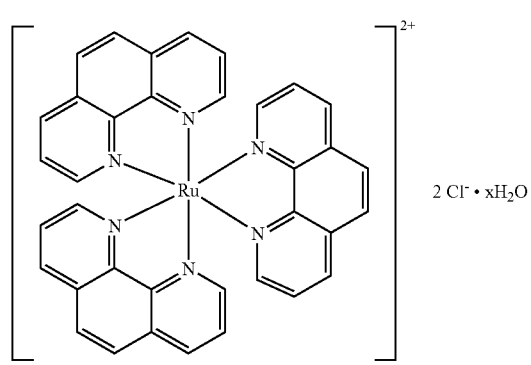

Ruthenium tris-(1,10-phenantroline) dichloride

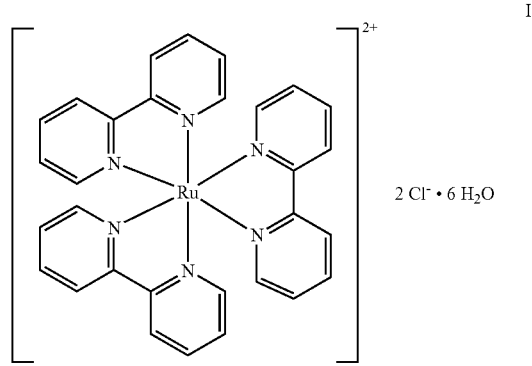

Ruthenium tris-(2,2'-bipyridyl) dichloride

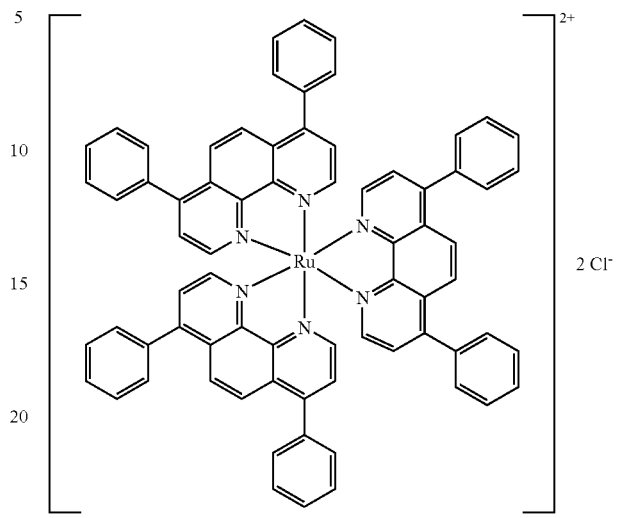

Ruthenium tris-(4,7-diphenyl-1,10-phenantroline) dichloride

As coating material inorganic-organic hybrid materials are used with adjusted chemical and physical properties by specific choice of appropriate precursor compounds. By the incorporation of special anchor groups such as amino, carboxyl, epoxide or sulphur for the absorption, adsorption or chemical fixation of sensor molecules and enzymes a new type material with enhanced stability against diffusion or bleaching of the sensitive molecules will become available for construction of optical transducer. Due to the compatibility of the new materials with glass surfaces, they are expected to exhibit a well-defined adhesion on silica optical fibre and to contribute significantly to the mechanical stability of the coated silica fibre. This effect and the inherent thermal and chemical stability of the inorganic backbone of the materials will be advantageous for the stability of the sensor system when the fibre comes into contact with solutions to be monitored in the reaction vessel. Further advantage of using these inorganic-organic hybrid materials in the construction of sensors is their high thermal stability and chemical durability— in comparison to commercially available standard pure organic acrylic coatings—due to the inorganic siloxane backbone in addition with organic crosslinking. This is important since it will permit much wider range of sensor sterilisation methods to be used on fibre-optic sensors compared to electrochemical sensors.

EXAMPLE 1

Coatings

Examples of sensitive coatings for optical detection of glucose in combination with oxygen for the double layer sensor and the single layer sensor are given in Tab. 2a, 2b (double layer) and Tab. 3 (single layer).

TAB 2a

| | KSK 1343-I or KSK 1301 | KSK 1343-II | KSK 1343-III | KSK 1344-I or KSK 1301-I | KSK 1344-II | KSK 1344-III | KSK 1345-I or KSK 1301-II | KSK 1345-II | KSK 1345-III |
|---|---|---|---|---|---|---|---|---|---|
| | | | | Primary Coating | | | | | |
| Composition | 13, 23 — 1% Ru-1 | 13, 23 — 3% Ru-1 | 13, 23 — 5% Ru-1 | 13, 23 25% 16 1% Ru-1 | 13, 23 25% 16 3% Ru-1 | 13, 23 25% 16 5% Ru-1 | 13, 23 50% 16 1% Ru-1 | 13, 23 50% 16 3% Ru-1 | 13, 23 50% 16 5% Ru-1 |
| | | | | Secondary Coating | | | | | |
| Composition | 34 | 34 | 34 | 34 | 34 | 34 | 34 | 34 | 34 |

TAB 2b

| | KSK 1349-I or KSK 1311 | KSK 1349-II | KSK 1349-III | KSK 1350-I or KSK 1311-I | KSK 1350-II | KSK 1350-III | KSK 1351-I or KSK 1311-II | KSK 1351-II | KSK 1350-III |
|---|---|---|---|---|---|---|---|---|---|
| | | | | Primary Coating | | | | | |
| Composition | 7, 15, 22, 24 — 1% Ru-1 | 7, 15, 22, 24 — 3% Ru-1 | 7, 15, 22, 24 — 5% Ru-1 | 7, 15, 22, 24 25% 16 1% Ru-1 | 7, 15, 22, 24 25% 16 3% Ru-1 | 7, 15, 22, 24 25% 16 5% Ru-1 | 7, 15, 22, 24 50% 16 1% Ru-1 | 7, 15, 22, 24 50% 16 3% Ru-1 | 7, 15, 22, 24 50% 16 5% Ru-1 |
| | | | | Secondary Coating | | | | | |
| Composition | 34 | 34 | 34 | 34 | 34 | 34 | 34 | 34 | 34 |

TAB 3

| | KSK 1393-IV | KSK 1393-V | KSK 1393-VI | KSK 1416-IV | KSK 1416-V | KSK 1416-VI | KSK 1417-IV | KSK 1417-V | KSK 1417-VI |
|---|---|---|---|---|---|---|---|---|---|
| | | | | Single Coating | | | | | |
| Composition | 24, 41 — 1% Ru-1 | 24, 41 — 3% Ru-1 | 24, 41 — 5% Ru-1 | 24, 41 25% 16 1% Ru-1 | 24, 41 25% 16 3% Ru-1 | 24, 41 25% 16 5% Ru-1 | 24, 41 50% 16 1% Ru-1 | 24, 41 50% 16 3% Ru-1 | 24, 41 50% 16 5% Ru-1 |

| | KSK 1349-I or KSK 1311 | KSK 1349-II | KSK 1349-III | KSK 1350-I or KSK 1311-I | KSK 1350-II | KSK 1350-III | KSK 1351-I or KSK 1311-II | KSK 1351-II | KSK 1350-III |
|---|---|---|---|---|---|---|---|---|---|
| | | | | Single Coating | | | | | |
| Composition | 7, 15, 22, 24 — 1% Ru-1 | 7, 15, 22, 24 — 3% Ru-1 | 7, 15 22, 24 — 5% Ru-1 | 7, 15, 22, 24 25% 16 1% Ru-1 | 7, 15, 22, 24 25% 16 3% Ru-1 | 7, 15, 22, 24 25% 16 5% Ru-1 | 7, 15, 22, 24 50% 16 1% Ru-1 | 7, 15, 22, 24 50% 16 3% Ru-1 | 7, 15, 22, 24 50% 16 5% Ru-1 |

Glass slides were dip coated and the (Meth)acrylic based hybrid coating material was UV cured (Hg radiation source, UV power ca. 1000-6000 mJ/cm$^2$). The procedure was similar for the primary and the secondary coating as well as for the single coating.

EXAMPLE 2

The Enzyme GOD 130 without Further Modification

The following procedures are possible to incorporate the enzyme GOD 130 into the secondary coating of the double layer structure:

1. 10% GOD 130 in 20 mM phosphate buffer, pH 7.5 mixed in proportion 1:2 with hybrid coating 34
2. 5% GOD 130 in hybrid coating 34.
3. 10% GOD 130 in hybrid coating 34.
4. 2 layers of 10% GOD 130 in hybrid coating 34.
5. immobilisation of GOD 130 with BSA under GA vapour (30 min).
6. 3% GOD in hybrid coating 34.
7. 2 layers of 3% GOD 130 in hybrid coating 34.
8. immobilisation of GOD 130 with BSA under Glutar aldehyde vapour (40 min).
9. 3% GOD 130 in mixture of hybrid coating 34 with water in proportion 1:1.

10. 5% GOD 130 in mixture of hybrid coating 34 with water in proportion 1:1.
11. 2 layers of 5% GOD130 in mixture of hybrid coating 34 with water in proportion 1:1.

The procedures 5, 8, 9, 10, 11 for incorporation of GOD in the secondary layer are most promising. The GOD 130 solutions are mixed with the solution of the secondary coating. The mixture is applied on the primary layer and UV cured.

Glucose Sensitivity, Measurement

Double coated microscopic glass slides (primary layer containing the Ru complex and secondary layer containing GOD 130) were put into an aerated measurement cell containing 500 ml of 10 mM phosphate buffer solution (pH=7). The fluorescence lifetime of the Ru complex was measured (directly indicating the consumption of oxygen according to the reaction scheme in Eqn. 1). In FIG. 1 the response to an aerobic (in air)-anaerobic (in nitrogen) change of conditions and response to an increase of glucose concentration (in range from 0 to 3 mM) are outlined.

Curve 1345-I (blue), measured in air:

Primary layer 1345-I:

consisting of components 13 (25 mole-%), 23 (25 mole-%), 16a (50 mole-%) and 1 weight-% Ru-1

Secondary layer:

component 34, containing GOD 130 (incorporated according to procedure 9)

Curve 1351-I (pink), measured in nitrogen:

Primary layer 1345-I:

consisting of components 7 (10 mole-%), 15 (2.5 mole-%), 22 (7.5 mole-%), 24 (30 mole-%), 16b (50 mole-%) and 1 weight-% Ru-1

Secondary layer:

component 34, containing GOD 130 (incorporated according to procedure 9)

Figure 2:
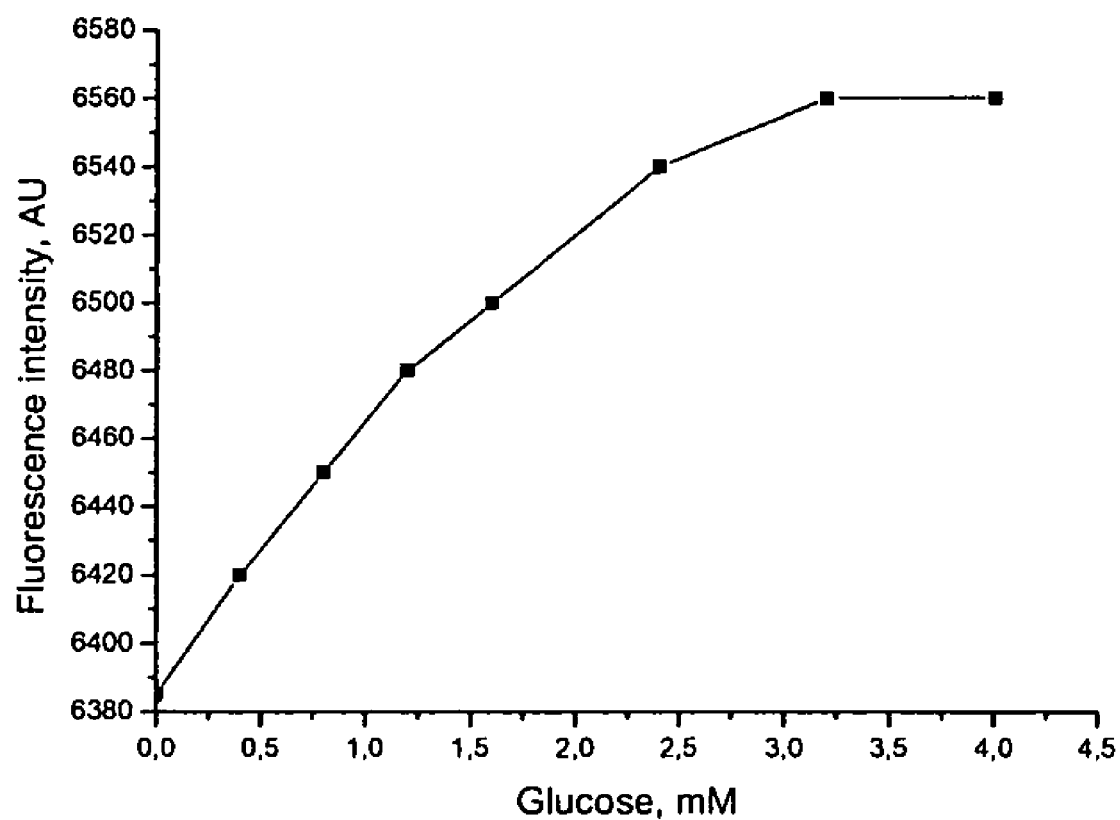
FIG. 2 depicts the increase of fluorescence intensity with increasing concentration of glucose.

In FIG. 2 the increase of the fluorescence signal with increasing concentration of glucose is shown.

EXAMPLE 4

The Enzyme GOD 130 after Further Modification

Aminated sepabeads with average particle size of 20 μm were purchased from Resindion SRL (Mitsubishi Chemical Corp.) Glucose oxidase was immobilized on the sepabeads as described in literature (Lorena Betancor, Fernando Lopez-Gallego, Aurelio Hidalgo, Manuel Fuentes, Ondrej Podrasky, Gabriela Kuncova, Jose M. Guisan, Roberto Fernandez-Lafuente, Biomacremolecules 6 (2005) 1027-1030).

Three types of sepabeads with immobilized glucose oxidase were used (s. Tab. 4):

Sepabeads ECEA2-60x 80A,

CLEA-60x-DYp and

ECEA2-60x

Sepabeads with immobilized glucose oxidase and hybrid coating material were mixed, coated on glass slides and finally the coatings were UV cured.

TAB 4

| | Sample no. | | |
|---|---|---|---|
| | 1 | 2 | 3 |
| Sepabeads | ECEA2-60x-80A | CLEA-60x | ECEA2-60x |
| $m_{sach}$ (mg) | 6.3 | 5.8 | 5.9 |
| $m_{sepa}$ (mg) | 50.2 | 54.1 | 50.8 |
| $m_{hyb}$ (mg) | 80.9 | 67.4 | 66.3 |

$m_{sach}$ amount of saccharose, $m_{sepa}$ amount of sepabeads with immobilized glucose oxi-dase $m_{hyb}$ amount of hybrid coating material consisting of components 7 (20 mole-%), 15 (5 mole-%), 22 (15 mole-%), 24 (60 mole-%) and 1 weight-% Ru-1

Glucose Sensitivity, Measurement

Single coated microscopic glass slides (one layer containing the Ru complex and the pre-immobilized GOD 130) were put into an aerated measurement cell containing 500 ml of 10 mM phosphate buffer solution (pH=7).

Figure 3:
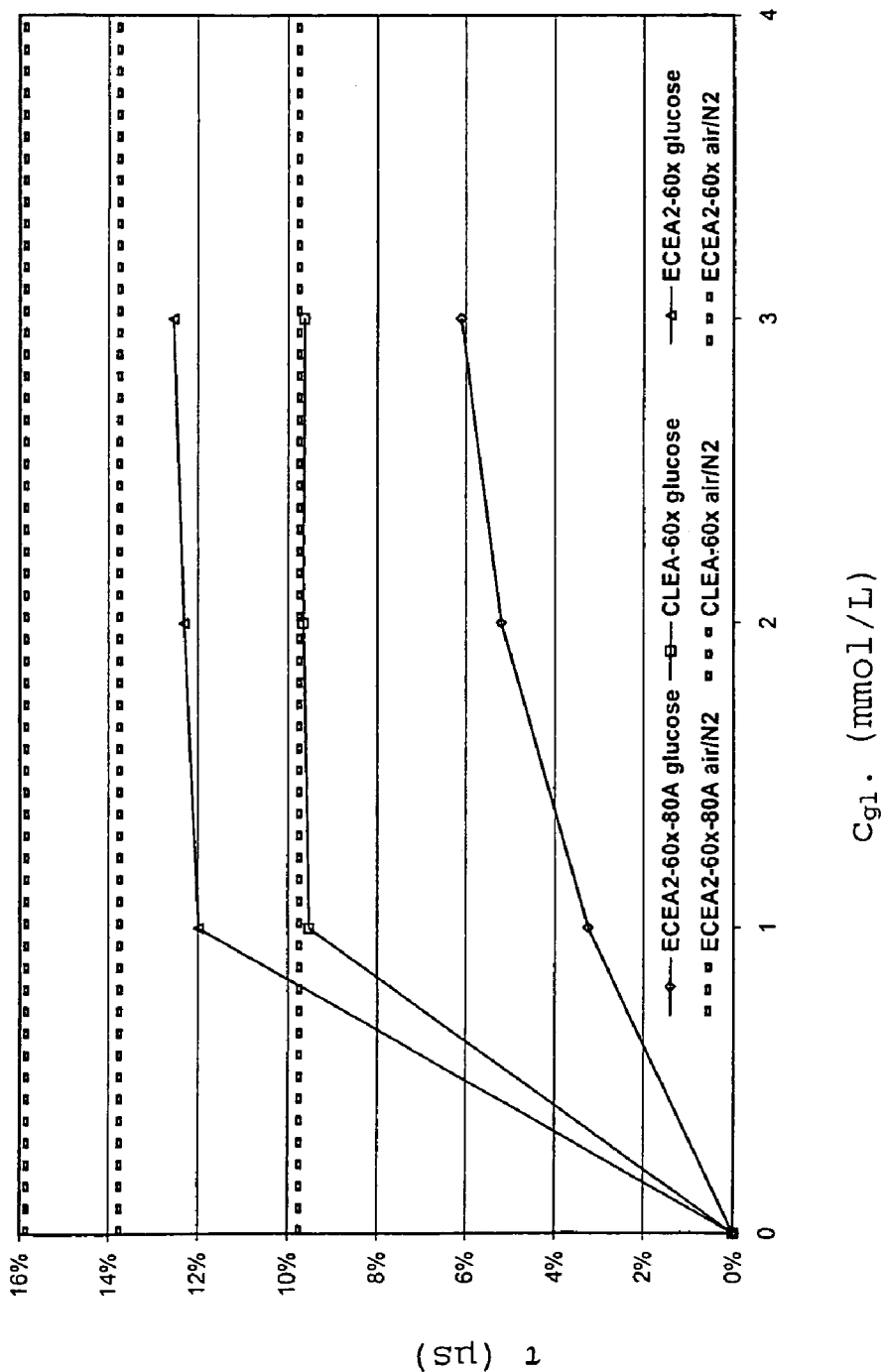
FIG. 3 depicts the relative change of fluorescence lifetimes as a function of glucose concentration. See Example 4.

The fluorescence lifetime of the Ru complex was measured (directly indicating the consumption of oxygen according to the reaction scheme in Eqn. 1). In FIG. 3 the relative change of fluorescence lifetimes is shown as a function of glucose concentration (in range from 0 to 3 mM).

The invention claimed is:

1. A biosensor comprising a substrate with at least one coating of an inorganic-organic hybrid polymer as a matrix for at least one Ruthenium complex selected from the group consisting of Ruthenium tris-(2,2'-bipyridyl) dichloride (II):

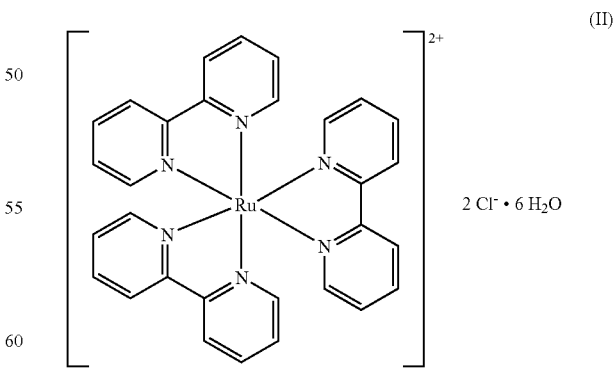

and Ruthenium tris-(4,7-diphenyl-1,10-phenanthroline) dichloride (III):

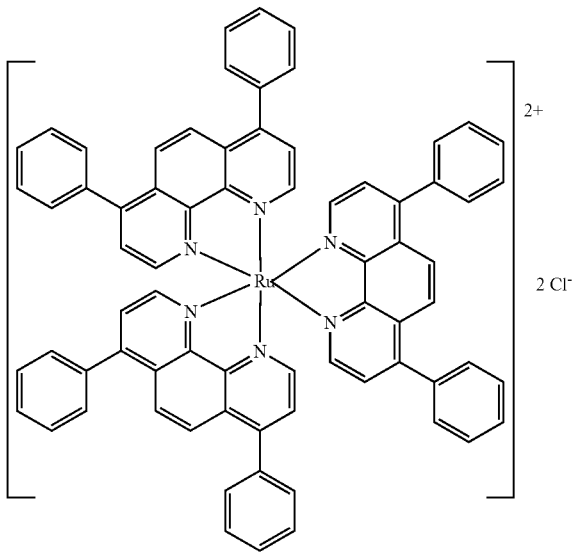

and at least one enzyme
wherein the inorganic-organic hybrid polymer is obtained by hydrolytic condensation of at least one organically substituted alkoxysilane and at least one alkoxy compound of a metal and an additional organic network is formed by polymerization of reactive groups.

2. The biosensor of claim 1, wherein the substrate is a glass and/or a polymer.

3. The biosensor of claim 1, wherein the substrate is an optical lens or an optical fibre.

4. The biosensor of claim 1, wherein the substrate is an optical fibre having a cladding layer.

5. The biosensor of claim 1, wherein the enzyme is selected from the group consisting of glucose oxidase from *Penicillinium vitale*, glucose oxidase from *Aspergillus niger*, glucose oxidase from *Aspergillus niger* type II and glucose oxidase from *Aspergillus niger* type IIS.

6. The biosensor of claim 1, wherein the enzyme is selected from the group consisting of glucose oxidase, glucose isomerase and glucose catalase.

7. The biosensor of claim 1, wherein the enzyme is selected from the group consisting of glycerokinase, L-Glycerol-3-phosphate and catalase.

8. The bio sensor of claim 1, wherein the enzyme is a stabilized enzyme.

9. The biosensor of claim 8, wherein the stabilized enzyme is an enzyme stabilized by immobilization in a polymeric host matrix.

10. The biosensor of claim 9, wherein the polymeric host matrix is selected from the group polystyrene, styrene/divinylbenzene copolymer and polyacrylics.

11. The biosensor of claim 1, wherein the alkoxy compound of a metal is selected from the group consisting of $Si(OEt)_4$, $Ti(OEt)_4$, $Zr(OPr)_4$ and $Al(O^sBu)_3$.

12. The biosensor of claim 1, wherein the substrate has a single coating comprising the at least one Ruthenium complex and the at least one enzyme.

13. The biosensor of claim 1, wherein the substrate has a first coating containing the at least one Ruthenium complex and a second coating containing the at least one enzyme.

14. The biosensor of claim 1, wherein the additional organic network is formed by the polymerization of monomers having reactive groups that are UV-curable.

15. The biosensor of claim 14, wherein the monomers are selected from the group consisting of glycidoxypropyltrimethoxysilane, vinyltrimethoxysilane, methacryloxypropyltrimethoxysilane, methacryloxypropylmethyl dimethoxysilane, acryloxypropylmethyl dimethoxysilane, N-(3-acryloxy-2-hydroxypropyl)-3-aminopropyltri-ethoxysilane, tripropyleneglycolacrylate trimethoxysilane, triethyleneglycolacrylate trimethoxysilane, tetraethyleneglycolacrylate trimethoxysilane, bisphenol-A-acrylate methyldimethoxysilane, glycerindimethacrylate triethoxysilane-a, glycerindimethacrylate triethoxysilane-b, butanediol-diglycidylether-diacrylate triethoxysilane-a, butanediol-diglycidylether-diacrylate triethoxysilane-b, propoxylated glyceryldiacrylate trimethoyxysilane, trimethylopropanediacrylate methyldimethoyxysilane, ethoxylated trimethylolpropane diacrylate trimethoxysilane, pentaerythritoltriacrylate triethoxysilane-a, and pentaerythritoltriacrylate triethoxysilane-b.

* * * * *